United States Patent
Harges, Jr. et al.

[11] Patent Number: 5,890,236
[45] Date of Patent: Apr. 6, 1999

[54] FIREFIGHTER GOGGLES

[76] Inventors: Cordell Frank Harges, Jr., 12629 Loma Verde Dr., Victorville, Calif. 92392; Bert Rivera, 1707 S. Marengo Ave., Alhambra, Calif. 91803

[21] Appl. No.: 924,883

[22] Filed: Sep. 5, 1997

[51] Int. Cl.⁶ .................................................. A61F 9/02
[52] U.S. Cl. ...................................... 2/440; 2/442; 2/445
[58] Field of Search ............................ 2/455, 458, 5, 2/6.3, 426, 427, 428, 440, 442, 444, 452, 445

[56] References Cited

U.S. PATENT DOCUMENTS

| | | | |
|---|---|---|---|
| 1,225,116 | 5/1917 | Dunkelsberg | 2/440 |
| 1,310,119 | 7/1919 | Harper | 2/440 |
| 2,007,186 | 7/1935 | Farrell | 2/440 |
| 2,264,351 | 12/1941 | Willosn | 2/440 |
| 2,918,676 | 12/1959 | Matheson | 2/440 |
| 3,562,813 | 2/1971 | Origer | 2/5 |
| 4,852,189 | 8/1989 | Duggan | 2/452 |
| 5,341,516 | 8/1994 | Keim | 2/5 |

*Primary Examiner*—John J. Calvert
*Assistant Examiner*—Larry D. Worrell, Jr.
*Attorney, Agent, or Firm*—Rothwell, Figg, Ernst, & Kurz, P.C.

[57] ABSTRACT

A new and improved firefighting goggle has sealing members formed from fire-resistant cloth material which improves both the firefighter's comfort and safety. The sealing members are removably attached to edges of the eye cups by a groove extending along the face-contacting edges. The headband of the goggle is protected with fire- and high temperature-resistant fabric material and includes a connector, e.g., a side release snap buckle, that connects in the back of the firefighter's head to facilitate doffing and donning without removal of the firefighter's helmet.

15 Claims, 2 Drawing Sheets

FIREFIGHTER GOGGLES

The invention relates to goggles and, in particular, to firefighter goggles.

BACKGROUND OF THE INVENTION

For years, firefighters—and, in particular, wildland firefighters—have worn goggles borrowed from other industries to satisfy their need for eye protection. With respect to the construction of the goggles, the goggles currently being used by firefighters, e.g., wildland firefighters, have rubber or rubberized frames and straps made from rubber or other elastic material. The frame may include a foam gasket around the perimeter, similar to a ski mask, to form a seal between the goggles and the face.

In a wildland firefighting environment, it is common for firefighters to be trapped and overrun by out-of-control fires. In such a situation, in particular, where a firefighter is exposed to extreme heat, the foam gasket or the petroleum-based rubber of the goggle can melt, causing injury to the firefighter and reducing the ability of the goggles to shield the firefighter's eyes. Moreover, from a comfort standpoint, such rubber-framed goggles are extremely hot and cause profuse sweating, which leads to fogging of the lenses and hence obscuring of the firefighter's vision.

With respect to the manner in which conventional firefighter goggles are secured to the firefighter's head, one current method uses a helmet retainer ring which wraps around the outer circumference of the helmet. The goggles are secured to the retainer ring with elastic cords and thus rest on the back bill of the helmet. The advantage of this configuration is that the goggles can be pulled forward and secured over the eyes when necessary without having to remove the helmet, but the system tends to stretch the frame of the goggle, thereby degrading the seal the goggles provide around the eyes which allows flying debris to get into the eyes. Additionally, the elastic cords tend to get stretched out due to the thin, light duty elastic typically used.

Another common method of securing the goggles to the head is simply to use a conventional, single-piece rubber or elastic headband strap. This configuration provides a better seal than securing the goggles to the helmet does, but requires the firefighter to remove the helmet in order to doff or don the goggles—a procedure which wastes time and exposes the firefighter to increased risk.

SUMMARY OF THE INVENTION

The present invention provides a new and improved firefighter goggle which overcomes these disadvantages by providing novel, far safer (and more comfortable) means for sealing the goggles around the eyes and a better way of securing the goggles to the firefighter's head. Additionally, a novel means for attaching the sealing member to the frame of the goggle is provided. With our invention, a firefighter is safer and far more comfortable than with conventional goggles, sweating less and thereby being able to see better. Additionally, the novel method of attachment of the goggles allows the goggles to be doffed and donned quickly and easily while the firefighter still has his helmet on his head. Accordingly, the firefighter's safety is enhanced.

Thus, according to a first aspect of the invention, a firefighting goggle includes an eye-covering, eye-protecting face unit and a headband which extends from one end of the face unit to an opposite end of the face unit. The headband is configured to secure the face unit to the head of the firefighter. The face unit includes a sealing member extending along a face-contacting edge thereof, and the sealing member includes a fire-resistant, fabric material.

In preferred embodiments, the face unit is composed of a pair of eye cups joined together by a nose bridge member, much like a pair of swimming goggles. Each of the eye cups covers one of the firefighter's eyes and each of the eye cups has a sealing member extending along a face-contacting edge thereof. Preferably, the sealing member includes a tubular sock formed from the fire-resistant, fabric material, which sock encloses a rope of fire-resistant batting or filling. In a particularly preferred embodiment, the face unit has a groove that extends along the face-contacting edge and the sock also has a rope-like anchor member extending generally parallel to the fire-resistant batting or filling. The anchor member fits within the groove extending along the face-contacting edge of the face unit to anchor the sealing member to the face-contacting edge of the unit. The fire-resistant fabric material preferably is activated carbon cloth material, and the fire-resistant batting or filling also preferably is activated carbon material. Preferably, the sealing member is removably attached to the face unit.

In another aspect, a firefighting goggle according to the invention includes an eye-covering, eye-protecting face unit and a headband that extends from end of the face unit to an opposite end of the face unit and which is configured to secure the face unit to the head of the firefighter. The face unit includes a groove extending along an edge thereof and a sealing member extends along the edge of the face unit, the sealing member including a bead that fits within the groove to anchor the sealing member to the face unit.

In preferred embodiments, the face unit is formed as a pair of eye cups joined together by a nose bridge member, and each of the eye cups has a groove along an edge thereof with the sealing member anchored thereto by means of a bead fitting within the groove. Preferably, the sealing member is made from fire-resistant, fabric material and may form a tubular sock that encases a rope of fire-resistant batting or filling.

In yet another aspect of the invention, a firefighting goggle includes an eye-covering, eye-protecting face unit and a headband extending from one end of the face unit to an opposite end of the face unit to secure the face unit to the head of the firefighter. The headband is constituted by two straps of approximately equal length, one extending from each end of the face unit. The free strap ends are releasably connected by a connector which, when the strap members are connected, is positioned approximately in the center of the back of the firefighter's head. Preferably, the straps are formed from a core of elastic material surrounded by a sheath of stretchable, fire-resistant fabric material.

DETAILED DESCRIPTION OF THE INVENTION

Figure 1:
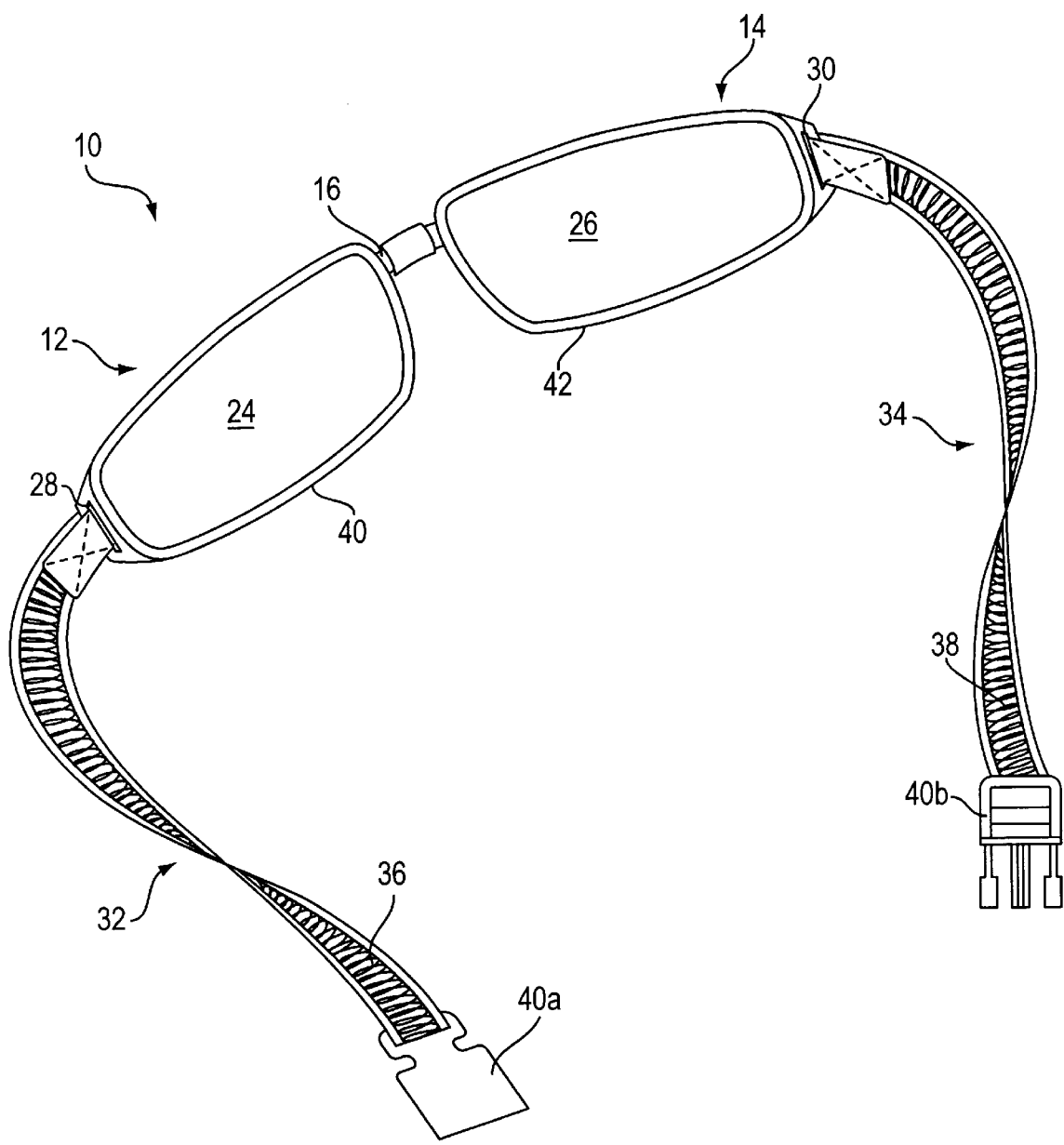
FIG. 1 is a perspective view of a firefighting goggle according to the invention.
Figure 2:
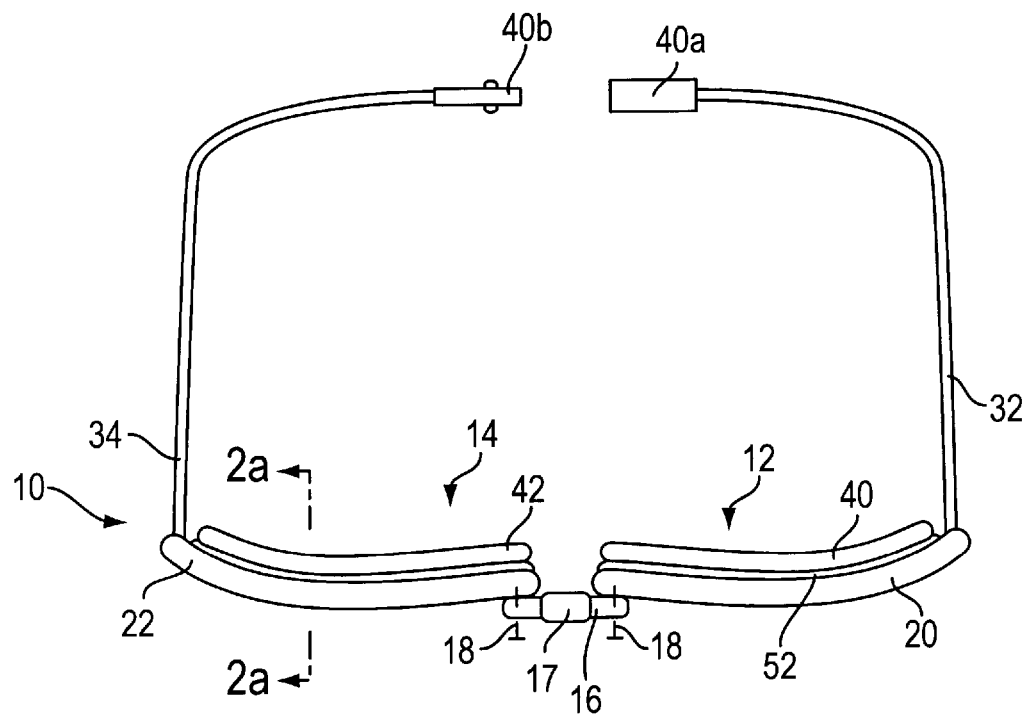
FIG. 2 is a top view of a firefighting goggle according to the invention.

A firefighter goggle 10 according to the invention is shown in FIGS. 1 and 2. The goggle 10 includes a pair of eye cups 12, 14 which are secured together by means of a flexible plastic nose bridge piece 16, which may be secured to the front of the eye cups 12, 14 by means of small hex-type set screws 18, as shown in FIG. 2. Preferably, the nose bridge piece has fire-resistant material 17 such as Nomex® and/or Kevlar® wrapped around it to protect it from high temperature and flame.

Each eye cup 12, 14 includes a frame member 20, 22 that is formed from a high strength, temperature-resistant material, e.g., polycarbonate, and a polycarbonate lens 24, 26. Each frame member has a slot 28, 30 through the outermost end thereof, and an elasticized strap member 32, 34 passes through each slot and is folded over and stitched down, snapped, clipped, or hook-and-loop fastened to itself as illustrated in FIG. 1.

Each strap member 32, 34 has a core of elastic material, and the core is enclosed in a lengthwise-extending pocket 36, 38 in a sheath of knit or otherwise stretchable fire-resistant material such as Nomex® and/or Kevlar®. The strap members each have one half 40a or 40b of a side-release snap buckle attached at the end thereof, preferably in a manner that allows the length of strap member between the eye cup and the buckle element to be adjusted. Preferably, enough strap material is provided such that the buckle is positioned in the center of the back of the firefighter's head, when the buckle halves are clipped together and the goggle is being worn, with enough extra strap material to adjust the fit. Furthermore, it is preferable for the buckle to have a flap-type covering made of fire-resistant material, e.g., Nomex® and/or Kevlar®, that can be secured over the buckle with a hook-and-loop closure (fire-resistant VEL-CRO® fastener or standard VELCRO® fastener) to protect the buckle from heat and flame.

Figure 2A:
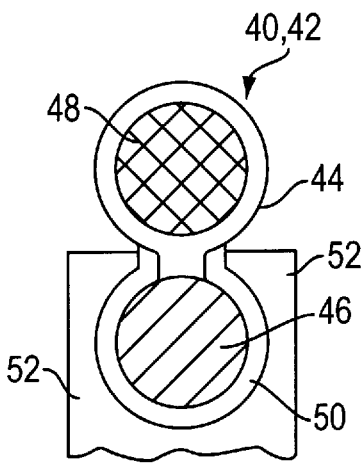
FIG. 2a is a section view along the lines 2a—2a in FIG. 2.

As shown in FIG. 2 and, in greater detail in FIG. 2a, each eye cup has a sealing member 40, 42 mounted to and extending along the perimeter edge thereof. In a preferred embodiment of our goggle, the sealing members 40, 42 are made from highly fire-resistant fabric, in contrast the rubber or silicone sealing skirts or foam sealing skirts that typically are used at present. Such material is more comfortable and will not melt on the firefighter's face.

In a particularly preferred embodiment, the sealing members 40, 42 are formed from a tubular sock 44 of knit or otherwise stretchy woven, highly fire-resistant material such as "activated carbon cloth," available, for example, from Micro Filtration Technologies located in Irvine, Calif. This fabric is not only extremely fire-resistant, but it also filters smoke, aldehydes, and other irritating vapors and keeps them from the firefighter's eyes. The sock 44 encases a length of plastic cording 46 and a "rope" of fire-resistant batting or fill material 48. The batting or fill material 48 can be made, for example, from activated carbon cloth material (fire-resistant or non-fire-resistant). The batting or fill material provides a cushioned sealing member which conforms closely to the firefighter's eye socket, thereby providing a secure seal. Moreover, because the material is relatively porous and "breathable," air is able to circulate through the eye cups, thereby helping to keep the firefighter's eye regions cooler than in the case of goggles with rubber or silicone sealing skirts.

As shown in FIG. 2a, the sealing members 40, 42 preferably are attached to the eye cup frames 20, 22 by inserting the plastic cording 46 into a groove 50 extending around the perimeter of each frame. The groove 50 may be formed in a rail 52 that extends from the main body of the eye cup frame, or alternatively, the groove may be formed in the frame member itself. Either way, the configuration shown in FIG. 2a allows the sealing members to be removed and replaced, e.g., if the sock material 44 becomes worn out or clogged with particulate debris to such an extent that air no longer can circulate through the eye cup.

Alternatively, in embodiments not shown, the plastic cording 46 could be eliminated and the sock 44 of fire-resistant material could be filled more fully with fire-resistant batting or fill material (or a smaller sock could be used), and the sealing members could be attached to the frame members with high temperature glue, pins, snaps, hook-and-loop fasteners, etc. Of these alternative attachment methods, the ones which allow the sealing members to be removed and replaced as the fabric becomes worn clearly are more preferable.

Other embodiments will of course occur to those having skill in the art. For example, although the preferred embodiment disclosed herein has separate eye cups like a pair of swimming goggles, the inventive concepts disclosed herein could be applied equally to a goggle that uses a unitary eye shield, much like a ski mask or scuba diving mask. Such other embodiments are deemed to be within the scope of the following claims.

We claim:

1. A firefighting goggle comprising:
    an eye-covering, eye-protecting face unit; and
    a head band extending from one end of said face unit to an opposite end of said face unit and configured to secure the face unit to the head of a firefighter;
    wherein said face unit includes a sealing member extending along a face-contacting edge thereof, said sealing member comprising a fire-resistant, fabric material.

2. The goggle of claim 1, wherein said face unit comprises a pair of eye cups joined together by a nose bridge member, each of said eye cups covering one of the firefighter's eyes and each of said eye cups having a sealing member extending along a face-contacting edge thereof.

3. The goggle of claim 1, wherein said sealing member comprises a tubular sock formed from said fire-resistant, fabric material.

4. The goggle of claim 3, wherein said sock encloses a rope of fire-resistant batting or filling.

5. The goggle of claim 4, wherein said face unit includes a groove extending along the face-contacting edge and wherein said sock also encloses a cording anchor member extending generally parallel to said rope of fire-resistant batting or filling, said anchor member fitting within said groove to anchor said sealing member to the face-contacting edge of said face unit.

6. The goggle of claim 1, wherein said fire-resistant fabric material comprises activated carbon cloth material.

7. The goggle of claim 4, wherein said fire-resistant batting or filling comprises activated carbon material.

8. The goggle of claim 1, wherein said sealing member is removably attached to said face unit to facilitate replacement of said fire-resistant fabric material.

9. A firefighting goggle comprising:
    an eye-covering, eye-protecting face unit; and
    a head band extending from one end of said face unit to an opposite end of said face unit and configured to secure the face unit to the head of a firefighter;
    wherein said face unit includes a groove extending along a face-contacting edge thereof and a sealing member extending along said face-contacting edge, said sealing member including a cording bead containing fire resistant material that fits within said groove to anchor said sealing member to said face unit and contacts the face of a firefighter.

10. The goggle of claim 9, wherein said face unit comprises a pair of eye cups joined together by a nose bridge member, each of said eye cups covering one of the firefighter's eyes and each of said eye cups having a groove extending along a face-contacting edge thereof and a sealing member anchored thereto by means of a cording bead fitting within said groove.

11. The goggle of claim 9, wherein said sealing member comprises fire resistant, material comprises a fabric.

12. The goggle of claim 11, wherein said sealing member comprises a tubular sock formed from said fire-resistant, fabric material and encasing a rope of fire-resistant batting or filling.

13. The goggle of claim 12, wherein said rope-like bead is formed by a cording member encased within said tubular sock.

14. A firefighting goggle according to claim 9:

an eye-covering, eye-protecting face unit; and wherein said head band comprises a pair of strap members of approximately equal length, one strap member extending from each end of said face unit, said strap members being releasably connected by a connector unit which, when said strap members are connected, is positioned approximately in the center of the back of the firefighter's head.

15. The goggle of claim 14, wherein said strap members each comprise a sheath of stretchable fire-resistant fabric material surrounding a core of elastic material.

* * * * *